Figure 1:
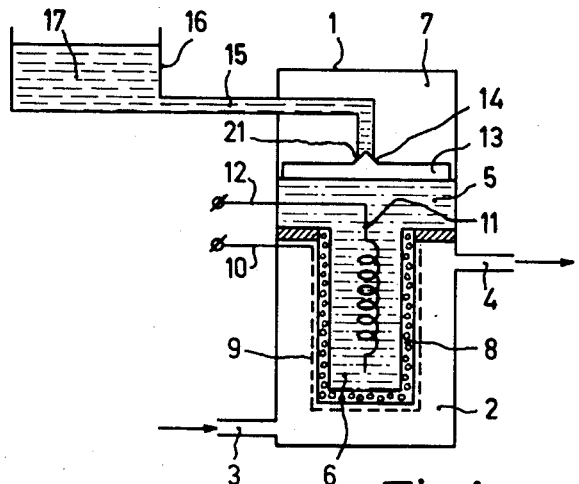

United States Patent [19]

Kruishoop

[11] 3,996,123
[45] Dec. 7, 1976

[54] COULOMETRIC DETECTOR

[75] Inventor: Johan Christiaan Willem Kruishoop, Eindhoven, Netherlands

[73] Assignee: U.S. Philips Corporation, New York, N.Y.

[22] Filed: Mar. 28, 1975

[21] Appl. No.: 562,964

[30] Foreign Application Priority Data

Apr. 8, 1974 Netherlands ............... 7404737

[52] U.S. Cl. ............................ 204/195 R; 204/1 T
[51] Int. Cl.² ..................................... G01N 27/46
[58] Field of Search ................... 204/1 T, 195 R

[56] References Cited

UNITED STATES PATENTS

| | | | |
|---|---|---|---|
| 2,370,871 | 3/1945 | Marks | 204/195 R |
| 3,361,661 | 1/1968 | Schulze | 204/1 T |
| 3,756,923 | 9/1973 | Dahms | 204/1 T |
| 3,761,377 | 9/1973 | Mang | 204/195 R |
| 3,824,166 | 7/1974 | Deibert | 204/195 R |

FOREIGN PATENTS OR APPLICATIONS 1,093,874  12/1967  United Kingdom ........... 204/195 R

*Primary Examiner*—T. Tung
*Attorney, Agent, or Firm*—Frank R. Trifari; Bernard Franzblau

[57] ABSTRACT

The proposed coulometric detector is of the "flow-past" type, in which the gas stream with the components to be measured is led past a surface which is covered with an electrolytic liquid. As reaction surface the outer surface of a porous layer is selected, which at the inner surface is in contact with a supply of electrolyte. To protect the detector against drying out, not the electrolyte, but the solvent, which is generally water, is supplied from a storage vessel. Steps are specified which allow the detector to take the form of a miniature measuring cell in mobile or stationary measuring stations for air pollution.

10 Claims, 2 Drawing Figures

COULOMETRIC DETECTOR

The invention relates to a coulometric detector for measuring traces of a component in a gaseous mixture, which detector comprises a housing with a first compartment, provided with a supply connection and a discharge connection for the gaseous mixture, and a second compartment, which is separated from the first compartment by low permeability membranes for passing an electrolyte which is stored in the second compartment, which contains a solvent for substances which react with said component and which is in contact with measuring electrodes, of which at least one electrode is present in the second compartment as an internal electrode and one electrode in the first compartment as an external electrode.

Such a coulometric detector or measuring cell is known from British patent specification No. 1.093,874.

Said Patent Specification states that components in a gaseous mixture can be measured by passing said mixture over a surface which is covered with an electrolytic liquid, a current being available at the measuring electrodes, which current is produced as a result of the reaction of the relevant gaseous components with the ions which are present in the solvent of the electrolyte. Problems associated therewith are: contamination of the reaction surface and evaporation of the electrolytic liquid. The British patent specification No. provides a solution to these problems, viz. by disposing the reaction surface vertically and passing the electrolyte along the surface. For this purpose an additional storage vessel with electrolyte is provided, which by means of a porous layer provides a dosaged flow at the reaction surface. The electrolyte collects at the underside of the reaction surface and subsequently drips off said surface.

A disadvantage of this approach is that a substantial amount of electrolyte must be stored and that the consumption of electrolyte is high. Moreover, steps must be taken to discharge the electrolyte in a suitable manner without influencing the supplied gas stream to be measured. A vertical arrangement of the cell is necessary.

The invention is based on the recognition that the contamination problem can be solved by selecting the outer surface of a porous layer as the reaction surface, the inner surface being in contact with a supply of electrolyte, and that it is not the electrolyte which evaporates, but the solvent, so that it suffices to supply only the solvent from a storage vessel.

A coulometric detector in accordance with the invention is characterized in that only one porous layer is provided as a low-permeability membrane, that the external electrode covers said layer completely but leaves the pores of the porous layer free, that the electrolyte partly fills the second compartment and furthermore that in the second compartment a supply tube terminates above the electrolyte level, which tube is connected to a storage vessel with solvent to replenish the solvent which is lost by evaporation.

Advantages of the invention are that only a small amount of electrolyte need be present in the cell, the external electrode makes proper contact with the electrolyte, contaminations can readily diffuse to the store of electrolyte through the pores of the porous layer, the detector is extremely suitable for miniaturisation, while for example only 1 cm³ of electrolyte is present, and, if necessary, a thermostatic control for maintaining the cell at a uniform temperature can be provided with few means, a very simple feature is provided to protect the detector against drying out. Also, the position of the cell relative to the vertical is non-critical so that the cell is extremely suitable for mobile measuring equipment.

It is to be noted that when a flow-through cell is defined as a cell which contains a fairly large amount of electrolyte through which the gas is passed in the form of bubbles, the advantages of a "flow-past cell" according to the invention with respect to a "flow-through cell" are: the noise in the measuring signal can be reduced by a factor of 10, for example 0.5 ppb relative to 5 ppb (1 ppb is 1 part in 1000 million parts), the gas-flow resistance is smaller so that the gas transport pump can be simple and cheap, the cell is not sensitive to shocks, and it is possible to divide the gas flow compartment into separate compartments which are each provided with a separate supply and discharge connection for a gas to be measured and with a separate outer electrode for the measuring signal.

In one embodiment of the detector according to the invention use is made of a siphon effect for automatically supplying the solvent to the electrolyte according to need, while the entire detector system is isolated from the surrounding.

This detector, according to the invention, is characterized in that the second compartment and the storage vessel are fully enclosed and are connected by a tube, the space above the liquid level of the solvent in the storage vessel communicates with the first compartment, the tube is filled with the solvent and there is a difference in height between the termination of the tube in the second compartment and the liquid level in the storage vessel, which difference determines the degree of wetting of the porous layer in the first compartment.

A different embodiment is characterized in that the part of the second compartment which is filled with electrolyte is separated from the remaining part of the second compartment by a second porous layer.

The advantages of this feature are that transportability of the cell is further improved, the position of the cell is even less critical, and mixing of the supplied solvent and electrolyte takes places through diffusion via the second porous layer so that in the case of a sudden supply of the solvent the measurement is not disturbed owing to concentration differences in the electrolyte. This last-mentioned advantage is especially important in the case of miniature detectors.

Figure 2:
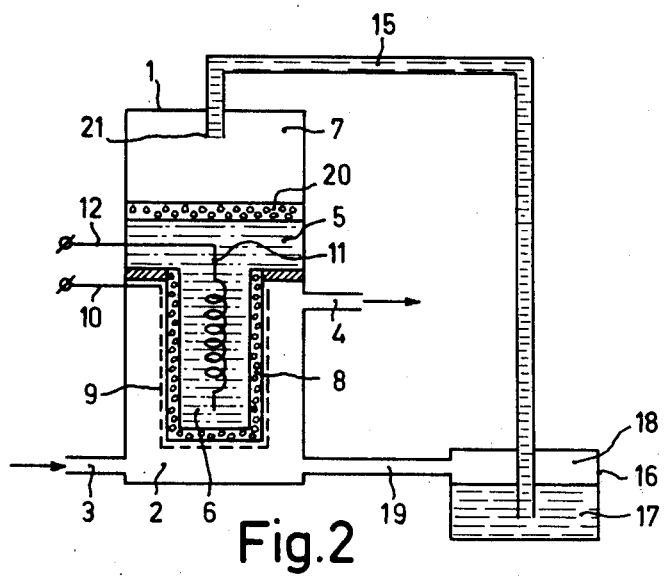

The invention will now be described in more detail with reference to the drawing, in which FIG. 1 represents a detector according to the invention, and FIG. 2 shows an embodiment of the detector according to the invention.

FIG. 1 schematically shows a coulometric detector according to the invention comprising a housing 1 including a first compartment 2 with a supply connection 3 and a discharge connection 4 for a gaseous mixture which contains components to be measured. The gas stream is passed through the detector by pumping means, not shown. The housing 1 is further divided into a second compartment 5, which is partly filled with an electrolytic liquid 6 above which a space 7 is situated. A porous membrane 8 separates the compartments 2 and 5. The membrane 8 is covered with an electrode layer 9 located at the side adjacent the compartment 2, which layer is connected to a measuring terminal 10. In the electrolyte 6 an electrode 11 is disposed, which is connected to a measuring terminal 12. The layer 8 allows the electrolyte to pass through so that the surface at the side which is located in compartment 2 is and remains wetted, but not to such an extent that the electrolyte drips off the porous layer 8. A proper wetting can be obtained by maintaining a pressure in the space 7 which is lower then the pressure in compartment 2. The layer 8 may be selected to be thin with wide pores so as to avoid inertia effects owing to diffusion in the layer. The electrode layer 9, which can be made of a noble metal such a gold or platinum, is for example applied to the porous layer 8 by vacuum-deposition or sputtering so that the pores remain open and proper electrical contact is ensured at all points where a reaction takes place between the ions of the electrolyte and the components to be measured of the gas stream. The gas stream, which is supplied at connection 3 and which is discharged at connection 4, flows over the outer surface of the porous layer 8. Then, in addition to said reaction which is to be measured electrically, the solvent of the electrolyte will evaporate at the surface of the layer 8 and will be carried along with the gas stream. As a result, the liquid level in compartment 5 will drop. This drop can be measured and, via space 7, more solvent can now be added to the electrolyte, in accordance with the invention, in order to restore the original liquid level. In FIG. 1 this is indicated by a simple detection element in the form of a float 13 with a valve 14 for the termination of a tube 15, which at one end terminates in space 7 and at the other end in a storage vessel 16 containing a solvent 17. It is to be noted that the solvent 17 is generally pure water.

FIG. 2 shows a fully closed detector system which is almost identical to that of FIG. 1, so that for the same components the same reference numerals are used. In the detector of FIG. 2 use is made of the vertical length of a liquid column in tube 15 for producing a reduced pressure in space 7. For this purpose the storage vessel 16 containing the solvent 17 is disposed at a point below the termination of tube 15 in space 7. As the tube 15 is not chosen too wide, the liquid column in tube 15 is maintained. When the electrolyte level in compartment 5 drops owing to evaporation of solvent in compartment 2, the pressure in space 7 decreases so that, owing to the suction and siphon action, liquid is supplied via tube 15 so as to restore the liquid level to its original value. It is necessary, however, that the pressure in compartment 2 and in the space 18 above the liquid level in vessel 16 be maintained constant, which can best be achieved by connecting space 18 to compartment 2 as is indicated in FIG. 2 by the connection 19.

In order to avoid the loss of electrolyte during transport of the detector because the electrolyte 6 splashes out of the compartment 5, whereby some electrolyte may be lost via compartment 2 or via tube 15, a porous layer 20 has been provided, which covers the electrolyte in compartment 5. Said layer 20 moreover has another important function which is essential, in particular with miniature detectors. As there should be no contact between the termination 21 and the electrolyte 6, in order to avoid diffusion in the direction of the storage vessel 16, the solvent 17 will be added to the electrolyte in drops, which drops fall from the termination 21 into the electrolyte. This may give rise to undesired local changes in concentration which affect the measuring results.

By catching these drops at layer 20, uniform mixing through diffusion will be achieved via the pores and channels of the porous layer 20.

The degree of wetting of the porous layer 8 can be adjusted for a satisfactory operation of the detector by varying the height of vessel 16 relative to housing 1.

What is claimed is:

1. A coulometric detector for measuring traces of a gas component in a gaseous mixture comprising, a housing having a first compartment provided with an inlet connection and a discharge connection for the flow of a gaseous mixture to be analyzed, said housing including a second compartment forming an electrolyte chamber partly filled with electrolyte and separated from the first compartment by a porous membrane for passing a controlled quantity of electrolyte sufficient to wet the membrane surface facing the first compartment but insufficient to allow electrolyte to drip off the membrane surface, said electrolyte containing a solvent for substances which react with said gas component when in contact with measuring electrodes, a first electrode disposed in the second compartment as an internal electrode and a second electrode disposed in the first compartment as an external electrode, the external electrode comprising a metal layer covering the membrane layer but in a manner so as to leave the pores of the porous membrane layer free, a supply tube terminating in the second compartment at a point above the electrolyte level, said tube being connected to a storage vessel containing only solvent to replenish any solvent which is lost by evaporation from the detector housing.

2. A coulometric detector for measuring traces of a component in a gaseous mixture comprising, a housing having a first compartment provided with an inlet connection and a discharge connection for the flow of a gaseous mixture to be analyzed, said housing including a second compartment forming an electrolyte chamber partly filled with electrolyte and separated from the first compartment by a porous membrane for passing an electrolyte stored in the second compartment, said electrolyte containing a solvent for substances which react with said component when in contact with measuring electrodes, a first electrode disposed in the second compartment as an internal electrode and a second electrode disposed in the first compartment as an external electrode, the external electrode comprising a metal layer covering the membrane layer but in a manner so as to leave the pores of the porous membrane layer free, a supply tube terminating in the second compartment at a point above the electrolyte level, said tube being connected to a storage vessel containing only solvent to replenish any solvent which is lost by evaporation from the detector housing, wherein the second compartment and the storage vessel are substantially closed to the surrounding environment, means coupling the space above the liquid level of the solvent in the storage vessel with the first compartment, the tube being filled with the solvent and arranged so that there is a difference in height between the termination of the tube in the second compartment and the liquid level in the storage vessel, which height difference determines the degree of wetting of the porous membrane layer in the first compartment.

3. A detector as claimed in claim 2, wherein the part of the second compartment which is filled with electrolyte is separated from the remaining part of the second compartment by a second porous layer.

4. A coulometric detector for measuring traces of a component in a gaseous mixture comprising, a housing having a first compartment provided with an inlet connection and a discharge connection for the flow of a gaseous mixture to be analyzed, said housing including a second compartment forming an electrolyte chamber partly filled with electrolyte and separated from the first compartment by a porous membrane for passing an electrolyte stored in the second compartment, said electrolyte containing a solvent for substances which react with said component when in contact with measuring electrodes, a first electrode disposed in the second compartment as an internal electrode and a second electrode disposed in the first compartment as an external electrode, the external electrode comprising a metal layer covering the membrane layer but in a manner so as to leave the pores of the porous membrane layer free, a supply tube terminating in the second compartment at a point above the electrolyte level, said tube being connected to a storage vessel containing only solvent to replenish any solvent which is lost by evaporation from the detector housing, and a second porous layer disposed within the second compartment so as to divide the second compartment into said electrolyte chamber containing a liquid electrolyte and a further chamber for receiving said supply tube, said solvent passing from the supply tube through the second porous layer to the electrolyte chamber.

5. A gas analyzer for determining a gas component in a gaseous mixture comprising, a housing, a membrane permeable to a liquid electrolyte and disposed within said housing to divide the housing into first and second chambers, said second chamber being partly filled with said liquid electrolyte, a first electrode disposed within the second chamber in contact with the electrolyte solution, a second electrode comprising a gas permeable layer of conductive material covering the surface of said membrane adjacent the first chamber so as to allow the electrolyte to pass through the pores of the membrane to wet the surface thereof adjacent the first chamber, said first chamber including a gas inlet and a gas outlet located so that the stream of gas mixture flows over the membrane surface, a reservoir containing only solvent for the electrolyte solution, and a supply tube coupling the reservoir to the second chamber at a point in the second chamber spaced apart from the liquid electrolyte contained therein.

6. A gas analyzer as claimed in claim 5 further comprising means responsive to the quantity of electrolyte liquid in the second chamber for automatically controlling the supply of solvent from the reservoir to the second chamber.

7. A gas analyzer as claimed in claim 5 wherein the degree of wetting of the surface of the membrane adjacent the first chamber is determined by the pressure in the unfilled space in the second chamber relative to the pressure in the first chamber.

8. A gas analyzer as claimed in claim 7 further comprising means coupling the first chamber to the reservoir for maintaining the first chamber and the space above the solvent liquid level in the reservoir at the same pressure.

9. A gas analyzer as claimed in claim 5 further comprising a second porous layer disposed within the second chamber so as to separate the part of the second chamber containing the liquid electrolyte from the remaining part of the second chamber, said supply tube terminating in said remaining part of the second chamber.

10. A gas analyzer as claimed in claim 5 further comprising first and second terminals external to said housing and electrically connected to said first and second electrodes, respectively, and wherein said second electrode layer is attached to and in contact with that surface area of the membrane containing the pores permeable to the passage of the electrolyte, said pores being arranged to restrict the passage of the liquid electrolyte in an amount such as to prevent the electrolyte from dripping off the membrane surface.

* * * * *